United States Patent
Tojo et al.

(10) Patent No.: US 7,052,714 B1
(45) Date of Patent: May 30, 2006

(54) OPHTHALMIC ADHESIVE PREPARATIONS FOR PERCUTANEOUS ADSORPTION

(75) Inventors: Kakuji Tojo, Iizuka (JP); Akiharu Isowaki, Akashi (JP)

(73) Assignees: Senju Pharmaceutical Co., LTD, Osaka (JP); Kakuji Tojo, Fukuoka (JP)

(*) Notice: Subject to any disclaimer, the term of this patent is extended or adjusted under 35 U.S.C. 154(b) by 0 days.

(21) Appl. No.: 10/089,431

(22) PCT Filed: Sep. 29, 2000

(86) PCT No.: PCT/JP00/06815

§ 371 (c)(1),
(2), (4) Date: Mar. 28, 2002

(87) PCT Pub. No.: WO01/26648

PCT Pub. Date: Apr. 19, 2001

(30) Foreign Application Priority Data

Oct. 13, 1999 (JP) .................................. 11-291002

(51) Int. Cl.
A61K 9/20 (2006.01)
A61K 13/00 (2006.01)

(52) U.S. Cl. .................. 424/449; 424/443; 424/445; 424/448

(58) Field of Classification Search ................ 424/448, 424/449, 443, 446, 489

See application file for complete search history.

(56) References Cited

U.S. PATENT DOCUMENTS

| 5,656,286 A | * | 8/1997 | Miranda et al. ............ 424/449 |
| 5,700,480 A | * | 12/1997 | Hille et al. ................. 424/448 |
| 5,869,086 A | * | 2/1999 | Deurer et al. .............. 424/449 |
| 6,086,911 A | * | 7/2000 | Godbey ...................... 424/448 |

FOREIGN PATENT DOCUMENTS

| EP | 0 771 565 A2 | * | 5/1997 |
| EP | 771 565 A2 |   | 5/1997 |
| EP | 0771565 A2 | * | 5/1997 |
| EP | 1 074 251 A1 |   | 2/2001 |
| JP | 63-218631 |   | 9/1988 |
| JP | 3-261720 |   | 11/1991 |
| JP | 5-255118 |   | 10/1993 |
| JP | 7-145061 |   | 6/1995 |

* cited by examiner

Primary Examiner—Gollamudi S. Kishore
Assistant Examiner—Micah-Paul Young
(74) Attorney, Agent, or Firm—Merchant & Gould P.C.

(57) ABSTRACT

Ophthalmic adhesive preparations for percutaneous absorption to be used in treating diseases in the posterior parts of eye characterized by having a drug-containing layer which contains a drug to be delivered to the posterior parts of eye including the crystalline lens, the vitreous body, the uvea and the retina, together with a percutaneous sorbefacient comprising polyoxyethylene oleyl ether and/or isopropyl myristate uniformly dispersed in a base matrix.

16 Claims, 7 Drawing Sheets

OPHTHALMIC ADHESIVE PREPARATIONS FOR PERCUTANEOUS ADSORPTION

TECHNICAL FIELD

The present invention relates to ophthalmic transdermal patches for treating diseases of the posterior segment of the eye including the lens, the vitreous body, the choroid, and the retina. More specifically, the present invention relates to ophthalmic transdermal patches comprising predetermined one or more percutaneous absorption enhancers for improving transfer of a drug to ophthalmic tissues.

BACKGROUND ART

After administration of a drug in the form of eye drops or by subconjunctival injection, the concentration of the drug generally would reach, relatively with ease, therapeutically effective levels in the anterior segment of the eye including the cornea and the anterior aqueous humor. However, in tissues in the posterior segment of the eye, including the lens, the vitreous humor, the choroid and the retina, which are located in deeper sites of the eye, the concentration of a drug generally would hardly, or almost never, reach therapeutically effective levels after its topical application either in the form of eye drops or by subconjunctival injection. Therefore, for diseases of the posterior segment of the eye, there have been tried different ways for administration of drugs, such as oral administration, intravenous drip, intravitreous injection or intravitreous implant, in order to deliver the drug to tissues of the posterior segment of the eye. For example, in clinical studies of aldose reductase inhibitors for treating diabetic retinopathy and of immunosuppressant cyclosporine for treating uveitis accompanying Behcet's disease, oral route has been employed to administer those drugs. Ganciclovir, for example, which has been clinically applied as a therapeutic for cytomegalovirus infection of the uvea and the retina, has been administered by intravenous drip or in the form of an intravitreous implant. Furthermore, inhibitors of fibrosis such as triamcinolone acetonide, 5-fluorouracil and mitomycin C have been studied as therapeutics for proliferative vitreoretinopathy, by the method of direct injection into the vitreous body.

However, for oral administration, those drugs generally must be taken several times a day, which would cause a concern about the patients' poor compliance. As to intravenous drip or intravitreous injection, on the other hand, indispensable frequent visit to the doctors would be a burden on the patients. Furthermore, with intravenous drip, there is a risk of causing side effects such as renal or hepatic disorders. Direct intravitreous injection could cause intravitreous hemorrhage or could damage the retina. Intravitreous implants need a surgical operation, which would imposes a burden on the patients and present risks entailed in a surgery.

As a system for administering a drug without imposing such a burden on patients, transdermal pharmaceutical preparations of estradiol and nicotine have been on the market. However, as for pharmaceutical preparations aimed to treat diseases localized in the eye by administering a drug through the skin, there is found only a report of a pilocarpine-containing transdermal preparation, which showed an intraocular pressure lowering effect comparable to that of pilocarpine eye drops (Japanese Laid-open Patent Application H8-509716). As a drug that has been used in the form of eye drops for inducing miosis to treat a specific type of glaucoma, pilocarpine is not required to act on the posterior segment of the eye. No attempt has been known before to deliver a drug to the posterior segment of the eye by making use of percutaneous absorption of the drug.

On this background, the objective of the present invention is to provide pharmaceutical preparations for delivering a drug to the posterior segment of the eye, that can eliminate the burden on the patients of frequent visit to the doctors or of a surgical operation, and that will make it easier to achieve improved patients' compliance.

DISCLOSURE OF INVENTION

Using drugs that, in light of their pharmacological effect, are desired to act on the very affected site of the posterior segment of the eye, the present inventors studied the transferability of the drugs to the eye by applying on the skin a base matrix containing them together with different compounds. As a result, the inventors found that the drugs can be delivered to the eye through the skin in other part of the body by enhancing percutaneous absorption of the drugs by utilizing certain proper compounds, and that polyoxyethylene oleyl ether and isopropyl myristate are particularly preferred percutaneous absorption enhancers for this purpose.

Thus, the present invention provides an ophthalmic transdermal patch for treating diseases of the posterior segment of the eye comprising a drug-containing layer uniformly containing in a base matrix a percutaneous absorption enhancer and a drug to be delivered to at least a part of the posterior segment of the eye including the lens, the vitreous body, the choroid and the retina.

The present invention further provides a method for treating a disease of at least a part of the posterior segment of the eye including the lens, the vitreous body, the choroid and the retina, in an animal, particularly a mammalian animal, and inter alia a human, wherein the method comprises applying to the animal an transdermal patch comprising a drug-containing layer uniformly containing in a base matrix an effective amount of a drug to be delivered to the part and a percutaneous absorption enhancer.

Examples of the drugs used in the present invention include, but are not limited to, anti-cataract agents, anti-inflammatory agents, anti-viral agents, immunosuppressants, calcium channel antagonists, glutamate receptor antagonists and cysteine protease inhibitors, which in general will hardly, or almost never, reach the posterior segment of the eye by topical instillation or subconjunctival injection. Specific examples include a variety of steroidal drugs represented by anti-inflammatory steroids, and the compound of the formula (1)

and a pharmaceutically acceptable salt thereof, wherein $R^1$ denotes C1–C4 alkyl, or C6–C10 aryl which may be substituted, $R^2$ and $R^3$ are the same or different from each other and denote hydrogen or C1–C4 alkyl, or are combined to form a C3–C7 ring, and $R^4$ denotes aryl, cycloalkyl, or a lower alkyl which may be substituted with an aromatic heterocyclic ring.

BEST MODE FOR CARRYING OUT THE INVENTION

The compound of the formula (1) is described with a number of specific examples of its synthesis and test examples regarding its calpain inhibiting activity and preventive effect on lens opacification in Japanese Laid-open Patent Application No. H10-147564, the entirety of which is incorporated in this application by reference. The compound may be prepared, for example, according to the following reaction scheme, wherein the abbreviations are as defined hereinbefore.

Examples of the sulfonyl chloride represented by the general formula (II) (hereinafter also referred to as "compound (II)") include naphthalenesulfonyl chloride, toluenesulfonyl chloride, fluorobenzenesulfonyl chloride, chloro-benzenesulfonyl chloride, methanesulfonyl chloride, bromobenzenesulfonyl chloride, and benzenesulfonyl chloride.

Examples of the compound represented by the general formula (III) (hereinafter also referred to as "compound (III)") include glycine, alanine, valine, D-valine, norvaline, leucine, isoleucine, norleucine, tert-leucine, 1-aminocyclopropanecarboxylic acid, 1-aminocyclobutanecarboxylic acid, 1-aminocyclopentanecarboxylic acid, and 1-aminocyclohexanecarboxylic acid. The reaction between the compound (II) and the compound (III) may be carried out by well known methods, e.g., Shotten-Bauman reaction and the like.

The condensation of the compound represented by the general formula (IV) and N-hydroxysuccinimide is carried out in a conventionally employed solvent (e.g. tetrahydrofuran, dichloromethane, chloroform, and ethyl acetate) using a condensation agent. Examples of condensation agents suitable for use include N, N-dicyclohexylcarbodiimide and 1-ethyl-3-(3-dimethylamiopropyl)carbodiimide hydrochloride. Examples of the amino-alcohol represented by the general formula (VI) (hereinafter also referred to as "compound (VI)") include valinol, leucinol, D-leucinol, phenylalaninol, tryptophanol, (S)-2-amino-3-cyclohexyl-1-propanol.

The reaction between the compound represented by the general formula (V) and the compound (VI) is carried out in a solvent such as tetrahydrofuran, dichloromethane, chloroform, ethyl acetate or the like, in the presence of a base (such as triethylamine, pyridine or the like). The compound (I) then may be prepared by oxidizing the compound represented by the general formula (VII) by an oxidizing agent (such as sulfur trioxide-pyridine complex, oxalyl chloride, pyridine chromate or the like). This reaction may be carried out at any desired temperature.

Within the scope of the compound thus obtained, examples of synthesis are described in the aforementioned patent document for the following species.

(1) N-(2-naphthalenesulfonyl)-L-valyl-L-leucinal,
(2) N-(4-fluorophenylsulfonyl)-L-valyl-L-leucinal,
(3) N-(4-chlorophenylsulfonyl)-L-valyl-L-leucinal,
(4) N-(4-methylphenylsulfonyl) -L-valyl-L-leucinal,
(5) N-(2-naphthalenesulfonyl)-L-tert-leucyl-L-leucinal,
(6) N-(4-fluorophenylsulfonyl)-D-valyl-L-leucinal,
(7) N-(4-fluorophenylsulfonyl)-L-norleucyl-L-leucinal,
(8) N-(4-fluorophenylsulfonyl)-L-norvalyl-L-leucinal,
(9) 1-(2-naphthalenesulfonylamino)cyclopentanecarbonyl-L-leucinal,
(10) N-(2-naphthalenesulfonyl)-L-tert-leucyl-L-phenylalaninal,
(11) N-(4-fluorophenylsulfonyl)-L-valyl-L-phenylalaninal, (12) N-(2-naphthalenesulfonyl)-L-valyl-L-phenylalaninal,
(13) N-(4-chlorophenylsulfonyl)-L-valyl-L-phenylalaninal,
(14) N-(4-methylphenylsulfonyl)-L-valyl-L-phenylalaninal,
(15) 1-(2-naphthalenesulfonylamino) cyclohexanecarbonyl-L-phenylalaninal,
(16) 1-(2-naphthalenesulfonylamino)cyclopentanecarbonyl-L-phenylalaninal,
(17) N-(4-chlorophenylsulfonyl)-L-valyl-L-tryptophanal,
(18) N-(4-fluorophenylsulfonyl)-L-valyl-L-tryptophanal,
(19) 1-(2-naphthalenesulfonylamino)cyclohexanecarbonyl-L-tryptophanal,
(20) N-(2-naphthalenesulfonyl)-L-tert-leucyl-L-tryptophanal,
(21) N-(4-fluorophenylsulfonyl)-L-valyl-L-cyclohexylalaninal,
(22) N-(2-naphthalenesulfonyl)-L-valyl-L-cyclohexylalaninal,
(23) N-(4-chlorophenylsulfonyl)-L-valyl-L-cyclohexylalaninal,
(24) N-(4-fluorophenylsulfonyl)-D-valyl-D-leucinal,
(25) N-(4-fluorophenylsulfonyl)-L-valyl-D-leucinal,
(26) N-(4-fluorophenylsulfonyl)-L-valyl-L-alaninal, and
(27) N-methylsulfonyl-L-valyl-L-leucinal In the same patent document, it is also reported that the compound possesses a cysteine protease inhibitor activity and therefore is useful as a drug for prevention or treatment of ischemic diseases, inflammation, cataract, retinopathy and the like. In the scope of the compound, examples particularly suitable to the purpose of the present invention include N-(4-fluorophenylsulfonyl)-L-valyl-L-leucinal or a pharmaceutically acceptable salt thereof.

In the present invention, especially suitable percutaneous absorption enhancers are, as mentioned, polyoxyethylene oleyl ether and isopropyl myristate, which may be used alone or in combination. When used alone, their content in the drug-containing layer is preferably in the range of 5–30 W/W % for polyoxyethylene oleyl ether, and 5–30 W/W % also for isopropyl myristate. Though they may be used in combination as desired, it is particularly preferable that the ratio of the content by weight concentration (W/W %) of polyoxyethylene oleyl ether to isopropyl myristate falls in the range of 1:0.1–1:5 in the drug-containing layer.

The content of polyoxyethylene oleyl ether in the drug-containing layer is more preferably 10–30 W/W %, still more preferably 10–20 W/W %, and most preferably 10–15 W/W %.

The content of isopropyl myristate in the drug-containing layer is more preferably 10–30 W/W %, still more preferably 10–20 W/W %, and most preferably 10–15 W/W %. Combined use of polyoxyethylene oleyl ether and isopropyl myristate further enhances percutaneous absorption of drugs.

In addition to polyoxyethylene oleyl ether and/or isopropyl myristate, the ophthalmic transdermal patches of the present invention may contain other supplementary percutaneous absorption enhancers known in the art. Examples of such percutaneous absorption enhancers include salts of N-acylsarcosine such as salts (sodium, potassium, magnesium, calcium, aluminum salts or the like) of N-lauroylsarcosine, cocoyl sarcosine, N-stearoylsarcosine, oleoylsarcosine, palmitoylsarcosine and the like, salts of higher fatty acids such as salts (sodium, potassium, magnesium, calcium, aluminum salts or the like) of capric acid, myristic acid, palmitic acid, lauric acid, stearic acid, palmitoleic acid, oleic acid, vaccenic acid, linolic acid, linolenic acid and the like, esters of higher fatty acids such as esters of capric acid, lauric acid, palmitic acid, stearic acid and the like with alcohols (methanol, ethanol, propanol, isopropanol, butanol, hexanol, pentanol, heptaneol and the like), hydroxydicarboxylic acids and dicarboxylic acids such as lactic acid, malic acid, tartaric acid, oxalic acid, malonic acid, succinic acid, glutaric acid, adipic acid, pimelic acid, suberic acid, azelaic acid, sebacic acid, fumaric acid, maleic acid and the like, monoterpenes such as 1-menthol, d-limonene and the like, surfactants such as sodium lauryl sulfate, sodium dodecylbenzensulfonate, sodium alkyldiphenylether-disulfonate, dioctyl sulfosuccinates, ammonium polyoxyalkyl phenyl ether sulfate and the like, alcohols such as ethanol, glycerol, diethylene glycol, propylene glycol, polyethylene glycol, higher alcohols and the like, dimethyl sulfoxide, alkyl or methyl derivatives of salicylic acid, urea, dimethylacetamide, dimethylformamide and the like, pyrrolidone derivatives such as polyvinylpyrrolidone, dodecylpyrrolidone, methylpyrrolidone and the like, and liquid vaseline, liquid paraffin, allantoin, squalene, Carbopol, vaseline, gelatin, amino acids, dodecylazacycloheptane-2-one and the like.

The base matrix that is particularly preferable comprises acrylic adhesives, silicone-based elastomers or styrene-isoprene-styrene copolymers, from which one can choose as desired. The matrix may be supported on a surface of one of supporting materials conventionally used in pharmaceutical preparations applied to the skin such as tapes, patches, poultices and the like, or any other support made of a material that will not affect the use of the present invention.

As for acrylic adhesive matrix, for example, acrylic copolymer resin PE-300 (solid content 40%), a product of NIPPON CARBIDE INDUSTRIES CO., INC., may be used as an adhesive, and CK-401 (solid content 10–15%), a product of NIPPON CARBIDE INDUSTRIES CO., INC., as a coagulation enhancer.

As for silicone-based matrix, for example, SLASTIC® MDX40-4210, a product of DOW CORNING ASIA, may be used as a silicone elastomer, and 360 MEDICAL FLUID, 20 cs, a product of DOW CORNING ASIA, as silicone oil. When providing an adhesive layer on the surface of the drug-containing layer comprising silicone-based matrix, for example, a silicone-based adhesive may be selected as desired from commercially available ones such as BIO-PSAQ7-4501 or BIO-PSAX7-4201, products of DOW CORNING ASIA, polymethylphenylsiloxane copolymer of LINTEC CORPORATION, or acrylic acid-dimethylsiloxane copolymer such as BPK-1, BPK-2 of WAKO PURE CHEMICAL INDUSTRIES, LTD. and the like.

As a styrene-isoprene-styrene copolymer, CARIFLEX TR-1107 and CARIFLEX TR-1111 of SHELL CHEMICAL, and JSR5000 of NIHON SYNTHETIC RUBBER are suitably used.

The concentration of the drug contained in the base matrix may be 1–20 W/W %, preferably 2–15 W/W %, and adjusted as desired in accordance with the disease to be treated and its severity.

In the polyoxyethylene oleyl ether used in the present invention, the average number of ethylene oxide added per oleyl moiety is preferably 4.4–5.5, and especially preferably about 5. It can be obtained by reacting oleyl alcohol with ethylene oxide having a hydroxyl group value of 4.5–5.5 as determined by the method described in the section of "Hydroxyl Group Value" in Testing Method for Fats and Oils in the Japanese Pharmacopoeia, 13th ed. For example, NOFABLE EAO-9905 of NOF CORPORATION may be favorably used.

The diseases of the posterior segment of the eye which are treated by the present invention are, for example, diseases of the lens, the vitreous body, the uvea including the choroid, or the retina, such as diabetic cataract, acute retinal necrosis syndrome, cytomegalovirus retinitis, intrinsic uveitis caused by autoimmune mechanism or abnormal immune response, proliferative vitreoretinopathy, diabetic retinopathy, retinal vessel occlusion, retinal periphlebitis, ischemic oculopathy, disorders of retinal vessels such as retinal aneurysm, retinopathy caused by ocular hypertension, nephropathy or hemopathy, retinal pigment epitheliopathy, retinal dystrophy, macular dystrophy, retinochoroidal atrophy, chorioretinopathy, macular dystrophy, macular edema, retinal pigment epithelium detachment, retinal detachment, degenerative retinoschisis, tumors such as retinoblastoma, retinal pigment epithelial tumor and tumor in optic disc capillary, optic neuropathy such as ischemic optic neuropathy, disc swelling such as choked disc and papilledema, open angle glaucoma, low tension glaucoma, angle closure glaucoma and the like.

Examples of drugs used in the present invention include aldose reductase inhibitors, corticosteroids (e.g. prednisolone, triamcinolone acetonide, dexamethasone), anti-viral agents (e.g., acyclovir, ganciclovir), immunosuppressants (e.g., cyclosporine), calcium ion channel antagonists (e.g., flunarizine, nifedipine, nicardipine), glutamate receptor antagonists (e.g., memantine, dizocilpine, dextrometorphan), and cysteine protease inhibitors [e.g., a compound represented by the formula (1), in particular N-(4-fluorophenylsulfonyl)-L-valyl-L-leucinal].

In use, the ophthalmic transdermal patches of the present invention may be applied at any location of the body surface as desired. It may be applied on a site relatively close to the eye, e.g., on the temple or around the eye, in particular on the skin of the eyelids or next to the lateral angle of the eye.

[Test Example]

The effect of transdermal patches of the present invention will be described below referring to test examples.

(1) Transdermal patches used

According to the formulas shown in Tables 1 and 2, transdermal patches were prepared containing prednisolone or N-(4-fluorophenylsulfonyl)-L-valyl-L-leucinal (hereinafter also referred to as "SJA6017"), respectively. In the tables, "%" means "W/W %" for the weight of the solid components. The concentration of the drugs (W/W %) were calculated as "drug/(drug + percutaneous absorption enhancers + acrylic adhesive + coagulation enhancer) × 100". EAO9905 indicates polyoxyethylene oleyl ether (NOFABLE EAO-9905: NOF CORPORATION) and IPM indicates isopropyl myristate.

Acrylic copolymer base matrix was prepared from an acrylic adhesive consisting of 40% acrylate copolymer solution in acetic acid and toluene (PE300: NIPPON CARBIDE INDUSTRIES CO., INC.) and a coagulation enhancer consisting of an approx. 7–10% cross-linking agent solution in ethyl acetate and toluene (CK401: NIPPON CARBIDE INDUSTRIES CO., INC.), by mixing and reacting the acrylate copolymer and the cross-linking agent at a ratio of 100:1 by weight.

(a) Formula of transdermal patches containing prednisolone

TABLE 1

| Preparation No. | Prednisolone (%) | EAO9905 (%) | IPM (%) | Acrylate copolymer (+ cross-linking agent) (%) |
|---|---|---|---|---|
| P1 (Control) | 3 | 0 | 0 | 97 |
| P2 | 3 | 10 | 10 | 77 |
| P3 | 3 | 10 | 20 | 67 |
| P4 | 3 | 20 | 10 | 67 |
| P5 | 3 | 20 | 20 | 57 |
| P6 | 3 | 5 | 0 | 92 |
| P7 | 3 | 10 | 0 | 87 |
| P8 | 3 | 20 | 0 | 77 |
| P9 | 3 | 0 | 10 | 87 |
| P10 | 3 | 0 | 20 | 77 |

(b) Formula of transdermal patches containing N-(4-fluorophenylsulfonyl)-L-valyl-L-leucinal

TABLE 2

| Preparation No. | SJA6017 (%) | EAO9905 (%) | IPM (%) | Acrylate copolymer (+ cross-linking agent) (%) |
|---|---|---|---|---|
| S1 (Control) | 5 | 0 | 0 | 95 |
| S2 | 5 | 20 | 0 | 75 |
| S3 | 5 | 20 | 10 | 65 |
| S4 | 5 | 20 | 20 | 55 |

(2) Device for percutaneous permeation experiment

Figure 1:
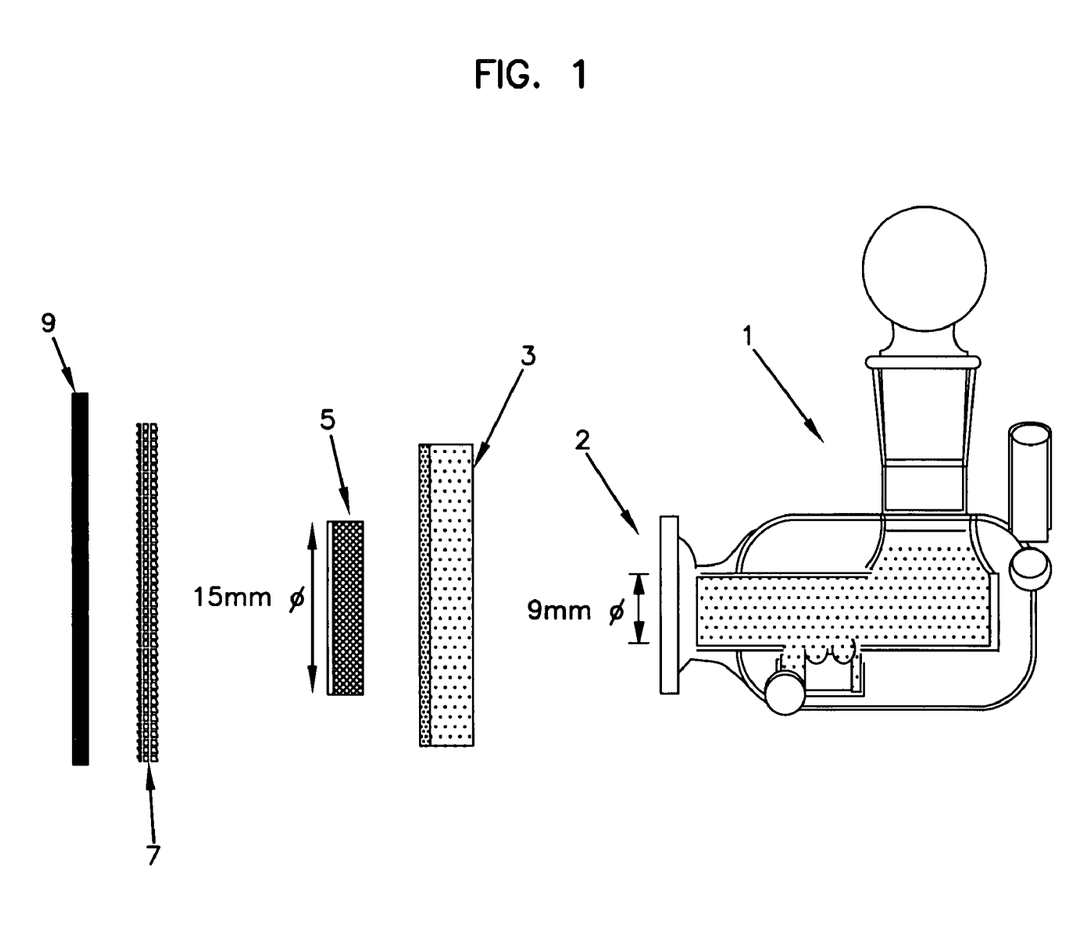
FIG. 1 is a schematic side view illustrating application of a piece of skin and a pharmaceutical preparation to one of the cells of a side-by-side type permeation experiment device.

In percutaneous permeation experiment, a side-by-side type cells, PERMCELL HK-5P (KOKURA GLASS KOGYO) was used as the permeation experiment device. FIG. 1 illustrates one of its symmetrical pair of cells. The effective area of the opening 2 to the cell 1 is 0.64 cm$^2$, and the effective capacity of the cell 1 is 5.0 ml. The water jacket of the device is connected to a circulating thermostatic bath by silicone tubing to keep the temperature of the cell interior at 37° C. The interior of the cell is constantly stirred with a magnetic stirrer (1200 rpm).

(3) Preparation of skin samples

Scratch-free abdominal skin of female hairless mice of 8 to 11-week old (Hr/Kud strain) was cut out and attached fat was removed using anatomical scissors.

(4) Drug permeation experiment using skin samples

Referring to FIG. 1, the skin 3 of the hairless mouse obtained above is applied to cover the opening 2 (0.64 cm$^2$) to the cell 1 (used as the receptor cell) of the side-by-side type diffusion cells. A transdermal patch 5 is applied on the skin. In order to keep it on the skin, the patch then is covered with a support net 7, which in turn is covered with an aluminum sheet 9. The other cell is placed over the sheet, with the openings to the cells aligned, and the cells are fixed with a holder. The receptor cell is filled with 40 W/W % PEG400 aqueous solution and kept at 37° C. At predetermined intervals, 100 μL samples are removed and the amount of the drug transferred to the receptor cell through the skin is determined by HPLC under the conditions indicated in (6) below. To keep the liquid volume in the receptor cell constant, the same amount of 40 W/W % PEG400 aqueous solution is supplemented after each sampling. Under these conditions, the permeability of the skin to a drug is kept substantially constant for at least 48 hours.

(5) In vivo test-1

Male Wistar/ST rats of 8-week old (body weight approx. 250 g), which had been removed of the hair, were used to examine the transfer of drugs from the transdermal patches to the plasma (prednisolone and SJA6017) and to the ocular tissues (prednisolone). For measuring transfer of the drugs into the plasma, cervical vein cannulation had been performed in advance to allow sampling of the blood over time. The above transdermal patches, No. P5 (prednisolone) and No. S4 (SJA 6017) with the surface area of 10 cm$^2$ were applied on the abdominal skin. 0.5-ml blood sampling was performed over time through a sampling port of the cannula placed on the occipital region of the rat's head. For measurement of transfer of the drug to the ocular tissues, rats were euthanized with an excess amount of sodium pentobarbital solution and the ocular tissues were removed. The tissues were pretreated, extracted and measured to determine the concentration of the drug by HPLC.

(6) In vivo test-2

A study of SJA6017-containing transdermal patch according to the formula below was made for examining transfer of SJA6017 from the patch to the plasma and to the ocular tissues, and comparison of the results with those from intravenous injection was also made.

| (Formula) | | |
|---|---|---|
| SJA6017 | 0.15 g | (5 W/W%) |
| EAO9905 | 0.6 g | (20 W/W%) |
| Isopropyl myristate | 0.6 g | (20 W/W%) |
| Acrylic adhesive (PE-300) | 1.6336 g | |
| Coagulation enhancer (CK-401) | 0.00165 g | |
| Total | 3.00 g | |

Male 9-week old Wistar/ST rats (body weight approx. 280–300 g), which had been removed of the hair, were used for the percutaneous absorption experiment. The hair was removed under anesthesia with a clipper and a shaver carefully to avoid injuring the skin. A SJA6017 transdermal patch having a drug-containing layer according to the above formula with the size of 5.0×6.0 cm (30 cm$^2$) was applied to the animals (n=10) of the percutaneous administration group on the abdominal skin and secured in position with a supporting tape to prevent it from falling. After 12 hours of application, the animals were sacrificed and the blood was collected from the abdominal aorta, and the plasma separated. The eyes were excised at the same time. Each of the eyes was separated into the aqueous humor, the lens and the other tissues (consisting of the cornea, the sclera, the iris-ciliary body, the vitreous body and the retina-choroid), and corresponding tissues separated from the 20 eyes were combined, respectively, to make a sample.

An intravenous administration experiment was carried out using 5 male Wistar rats (body weight approx. 600 g: 592±34 g) by administering 2 mg/kg SJA6017 through the tail vein of the animals under pentobarbital anesthesia. For the administration, a solution was used containing 10 mg SJA6017 dissolved in 10 ml mixture of ethanol/PEG400/water (1/2/1). Fifteen minutes after the intravenous administration, the animals were sacrificed, the blood was collected through the abdominal aorta, and the plasma separated. The eyes were excised at the same time. Each of the eyes was separated into the aqueous humor, the lens and the other tissues (consisting of the cornea, the sclera, the iris-ciliary body, the vitreous body and the retina-choroid), and corresponding tissues separated from the 10 eyes were combined, respectively, to make a sample.

(7) Determination of the concentration of the drugs in the samples (a) Determination of prednisolone concentration Determination of prednisolone (hereinafter also referred to as "PN") concentration in the samples was carried out by HPLC under the following conditions.

Column: CAPCELL PAK CN UG120 5 μm, 4.6 mm Ψ×250 mm

Guard column: CAPCELL PAK CN UG120 5 μm, 4.6 mm Ψ×35 mm

Detection: UV-254 nm

Mobile phase: acetonitrile/water=30/70

Flow rate: 1.0 ml/min

Temperature: 40° C.

Injection volume: 50 μor 100 μl

Retention time: approx. 6–7 minutes (b) Determination of the concentration of N-(4-fluorophenylsulfonyl)-L-valyl-L-leucinal Determination of the concentration of N-(4-fluorophenylsulfonyl)-L-valyl-L-leucinal in the samples was carried out by HPLC under the following conditions.

(i) In vitro test (concentration in the receptor cell)

Column: BECKMAN ULTRASPHERE ODS 5 μm 2.0 mm Ψ×250 mm

Detection: UV-250 nm

Mobile phase: 1% trifluoroacetic acid in a mixture of acetonitrile/water (35/65)

Flow rate: 0.25 ml/min

Temperature: 45° C.

Injection volume: 100 μl

Retention time: approx. 16 min (ii) In vivo test

Column: CAPCELL PAK C$_{18}$ SG120 5 μm 4.6 mm Ψ×250 mm

Detection: UV-272 nm

Mobile phase: 0.02 M phosphate buffer (pH 7):acetonitrile=45:55

Flow rate: 1.0 ml/min

Temperature: 40° C.

Injection volume: 100 μl

Retention time: approx. 14 min

[Test results]

<Test results obtained using percutaneous permeation experiment device>

Tables 3–6 and FIGS. 2–5 shows accumulative amounts (in μg/cm$^2$) of prednisolone and N-(4-fluorophenylsulfonyl)-L-valyl-L-leucinal (SJA6017) transferred into the receptor cell 36 or 42 hours after start of the tests using the percutaneous permeation experiment device.

Figure 2:
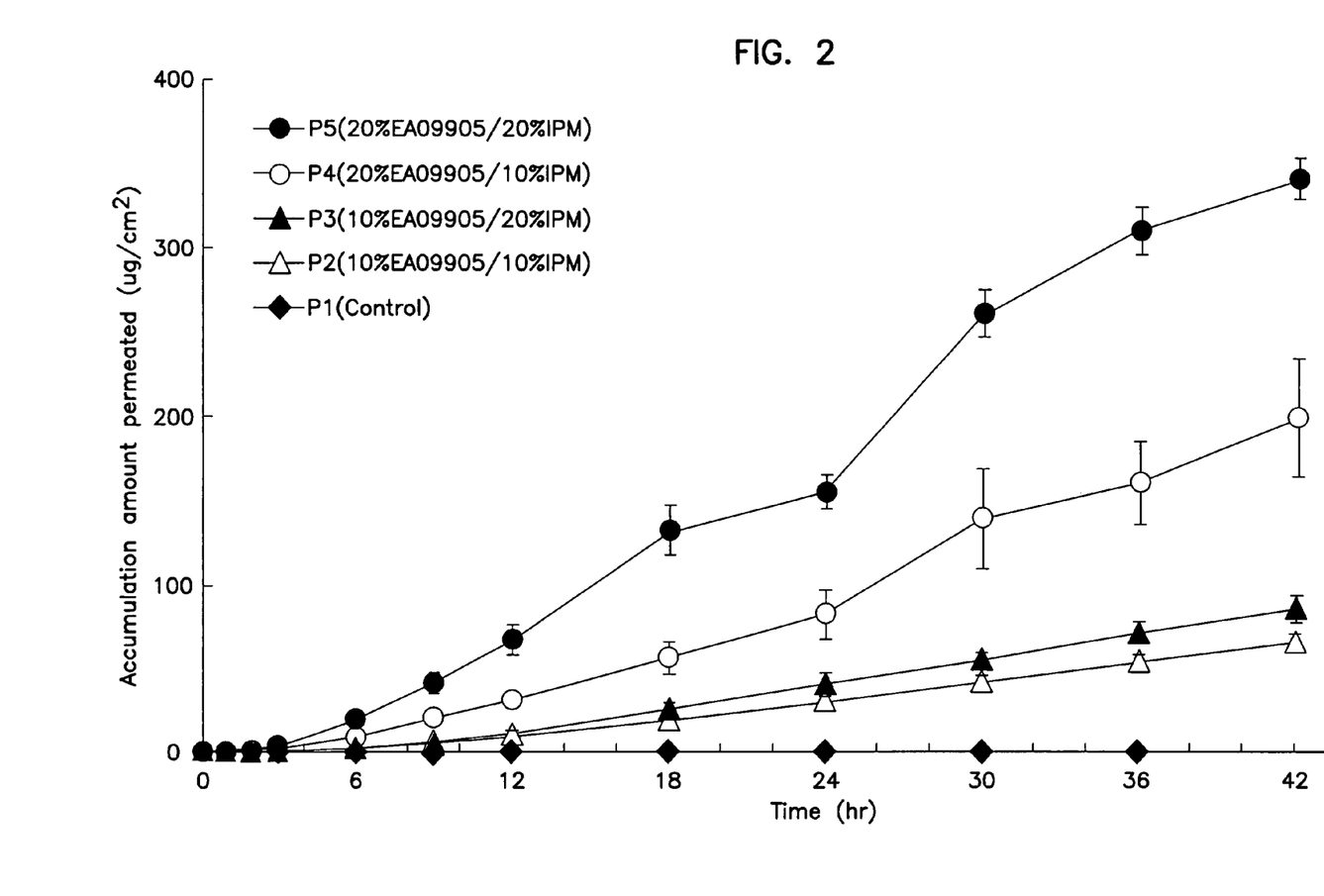
FIG. 2 is a graph showing in vitro prednisolone permeation through the skin with pharmaceutical preparations P2–P5.
Figure 3:
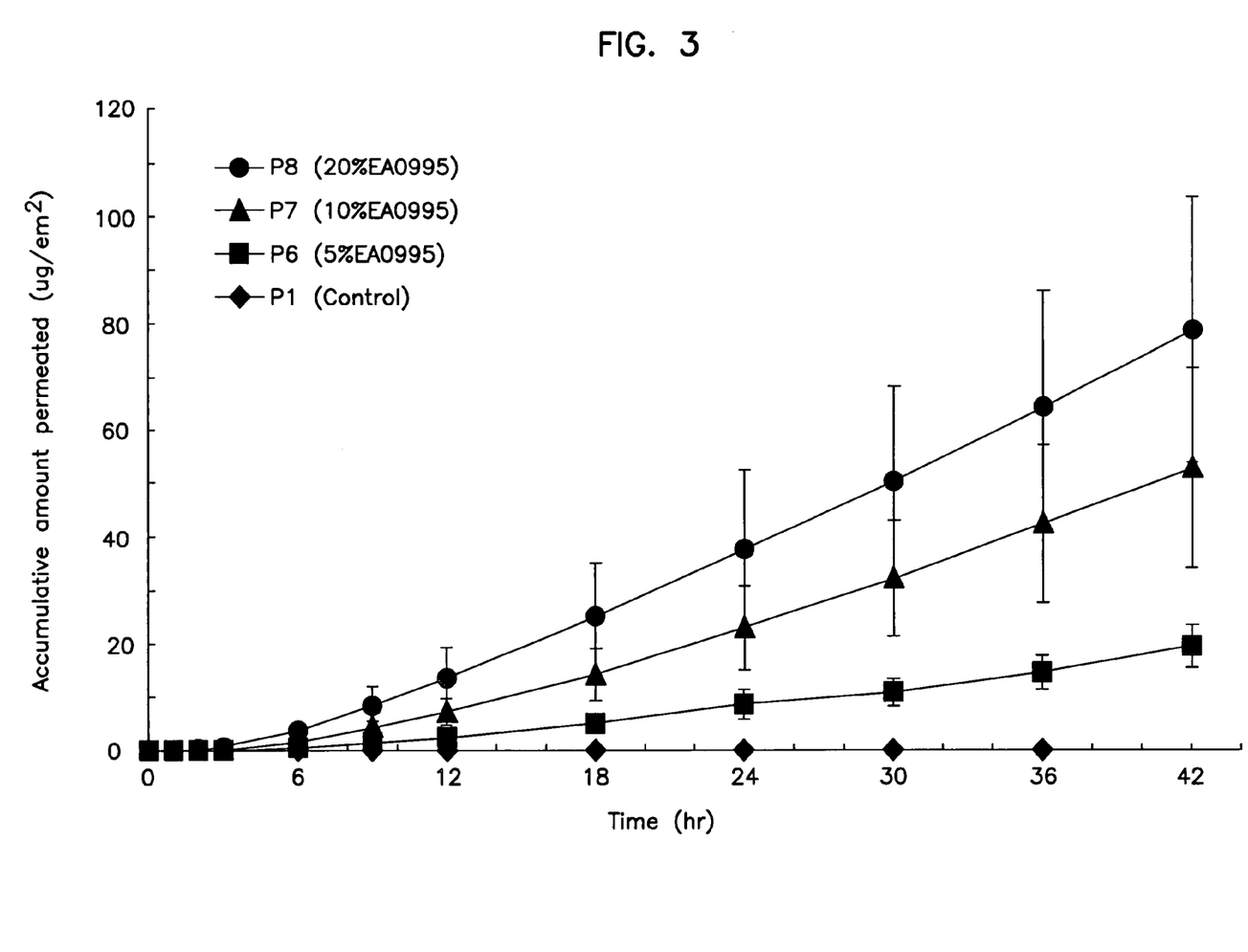
FIG. 3 is a graph showing in vitro prednisolone permeation through the skin with pharmaceutical preparations P6–P8.
Figure 4:
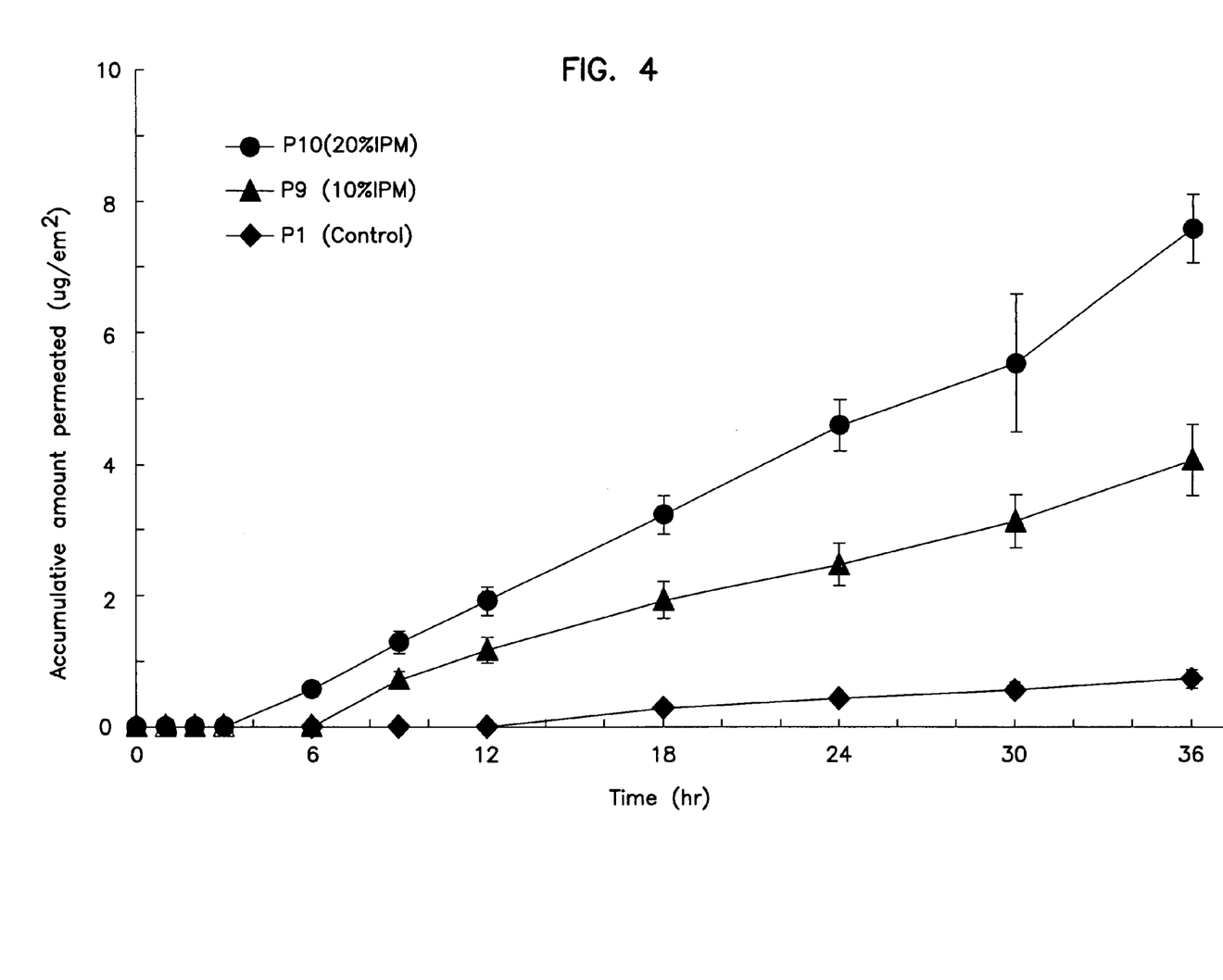
FIG. 4 is a graph showing in vitro prednisolone permeation through the skin with pharmaceutical preparations P9–P10.

As shown in Tables 3–5 and FIGS. 2–4, the percutaneous permeation of prednisolone from the transdermal patches P2–P10, which contained polyoxyethylene oleyl ether and/or isopropyl myristate, was greatly improved compared with the control (P1).

TABLE 3

| Time (hr) | P1 (Control) Mean | SD | P5 Mean | SD | P4 Mean | SD | P3 Mean | SD | P2 Mean | SD |
|---|---|---|---|---|---|---|---|---|---|---|
| 0 | 0.00 | 0.00 | 0.00 | 0.00 | 0.00 | 0.00 | 0.00 | 0.00 | 0.00 | 0.00 |
| 1 | 0.00 | 0.00 | 0.00 | 0.00 | 0.00 | 0.00 | 0.00 | 0.00 | 0.00 | 0.00 |
| 2 | 0.00 | 0.00 | 1.27 | 0.60 | 0.53 | 0.12 | 0.12 | 0.02 | 0.16 | 0.03 |
| 3 | 0.00 | 0.00 | 4.33 | 1.18 | 1.96 | 0.50 | 0.39 | 0.10 | 0.51 | 0.11 |
| 6 | 0.00 | 0.00 | 20.21 | 3.61 | 9.83 | 2.17 | 2.94 | 0.43 | 3.23 | 0.00 |
| 9 | 0.00 | 0.00 | 42.64 | 6.22 | 21.54 | 4.56 | 7.60 | 1.41 | 6.82 | 0.61 |
| 12 | 0.00 | 0.00 | 69.04 | 8.98 | 32.78 | 5.46 | 13.30 | 1.67 | 11.18 | 1.14 |
| 18 | 0.30 | 0.06 | 135.47 | 14.46 | 59.69 | 9.70 | 28.20 | 3.75 | 21.72 | 1.86 |
| 24 | 0.45 | 0.08 | 158.94 | 10.10 | 86.49 | 14.76 | 45.15 | 5.85 | 33.56 | 3.21 |
| 30 | 0.60 | 0.11 | 266.44 | 13.98 | 144.41 | 29.40 | 60.00 | 4.14 | 46.51 | 4.13 |
| 36 | 0.78 | 0.14 | 316.72 | 14.27 | 166.61 | 24.41 | 77.53 | 6.57 | 59.92 | 4.35 |
| 42 | — | — | 348.41 | 12.21 | 206.23 | 35.21 | 92.59 | 8.02 | 72.56 | 4.97 |

TABLE 4

| Time (hr) | P1 (Control) Mean | SD | P6 Mean | SD | P7 Mean | SD | P8 Mean | SD |
|---|---|---|---|---|---|---|---|---|
| 0 | 0.00 | 0.00 | 0.00 | 0.00 | 0.00 | 0.00 | 0.00 | 0.00 |
| 1 | 0.00 | 0.00 | 0.00 | 0.00 | 0.00 | 0.00 | 0.00 | 0.00 |
| 2 | 0.00 | 0.00 | 0.00 | 0.00 | 0.00 | 0.00 | 0.19 | 0.08 |
| 3 | 0.00 | 0.00 | 0.00 | 0.00 | 0.23 | 0.04 | 0.55 | 0.26 |
| 6 | 0.00 | 0.00 | 0.57 | 0.19 | 1.64 | 0.50 | 3.64 | 1.70 |
| 9 | 0.00 | 0.00 | 1.40 | 0.51 | 4.18 | 1.37 | 8.30 | 3.73 |
| 12 | 0.00 | 0.00 | 2.43 | 0.79 | 7.29 | 2.44 | 13.51 | 5.88 |
| 18 | 0.30 | 0.06 | 5.21 | 1.63 | 14.28 | 4.95 | 25.13 | 10.12 |
| 24 | 0.45 | 0.08 | 8.77 | 2.77 | 23.15 | 7.86 | 37.82 | 14.79 |
| 30 | 0.60 | 0.11 | 11.11 | 2.65 | 32.43 | 10.86 | 50.68 | 17.84 |
| 36 | 0.78 | 0.14 | 14.87 | 3.23 | 42.83 | 14.86 | 64.74 | 21.97 |
| 42 | — | — | 19.92 | 4.01 | 53.42 | 18.84 | 79.33 | 24.83 |

TABLE 5

| Time (hr) | P1 (Control) Mean | SD | P9 Mean | SD | P10 Mean | SD |
|---|---|---|---|---|---|---|
| 0 | 0.00 | 0.00 | 0.00 | 0.00 | 0.00 | 0.00 |
| 1 | 0.00 | 0.00 | 0.00 | 0.00 | 0.00 | 0.00 |
| 2 | 0.00 | 0.00 | 0.00 | 0.00 | 0.00 | 0.00 |
| 3 | 0.00 | 0.00 | 0.00 | 0.00 | 0.00 | 0.00 |
| 6 | 0.00 | 0.00 | 0.00 | 0.00 | 0.57 | 0.10 |
| 9 | 0.00 | 0.00 | 0.73 | 0.12 | 1.29 | 0.17 |
| 12 | 0.00 | 0.00 | 1.19 | 0.19 | 1.93 | 0.21 |
| 18 | 0.30 | 0.06 | 1.96 | 0.28 | 3.26 | 0.29 |
| 24 | 0.45 | 0.08 | 2.51 | 0.32 | 4.64 | 0.39 |
| 30 | 0.60 | 0.11 | 3.18 | 0.40 | 5.60 | 1.05 |
| 36 | 0.78 | 0.14 | 4.14 | 0.55 | 7.66 | 0.52 |

Figure 5:
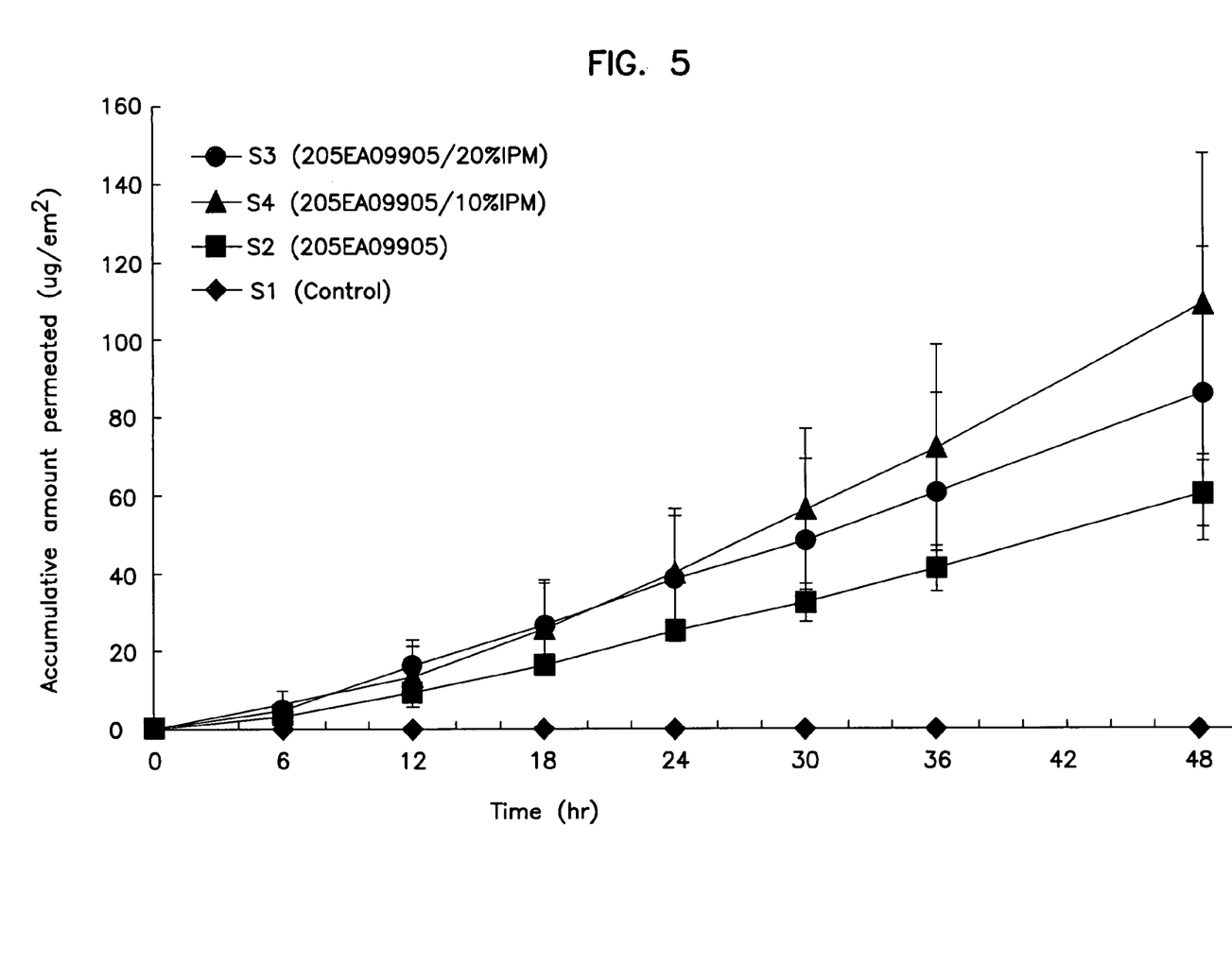
FIG. 5 is a graph showing in vitro SJA6017 permeation through the skin with pharmaceutical preparations S2–S4.

As to N-(4-fluorophenylsulfonyl)-L-valyl-L-leucinal, it is shown in Table 5 and FIG. 5 that percutaneous permeation was clearly noted with transdermal patches S2–S4 of the present invention while no percutaneous permeation was observed with the control (S1).

TABLE 6

| Time (hr) | S1 (Control) Mean | SD | S2 Mean | SD | S3 Mean | SD | S4 Mean | SD |
|---|---|---|---|---|---|---|---|---|
| 0 | 0.00 | 0.00 | 0.00 | 0.00 | 0.00 | 0.00 | 0.00 | 0.00 |
| 6 | 0.00 | 0.00 | 3.19 | 0.33 | 6.15 | 3.47 | 4.97 | 1.47 |
| 12 | 0.00 | 0.00 | 9.63 | 2.04 | 13.80 | 7.75 | 16.65 | 6.59 |
| 18 | 0.00 | 0.00 | 17.16 | 1.97 | 26.35 | 11.87 | 27.32 | 11.75 |
| 24 | 0.00 | 0.00 | 26.07 | 2.69 | 41.14 | 16.45 | 39.67 | 16.12 |
| 30 | 0.00 | 0.00 | 33.67 | 4.81 | 57.59 | 20.63 | 49.68 | 21.14 |
| 36 | 0.00 | 0.00 | 42.83 | 5.80 | 78.83 | 26.75 | 62.37 | 25.57 |
| 48 | 0.00 | 0.00 | 62.48 | 8.58 | 111.32 | 38.71 | 88.36 | 37.86 |

<The results of in vivo test>

(1) Plasma concentration of the drugs after application of transdermal patches (in vivo test-1)

Figure 6:
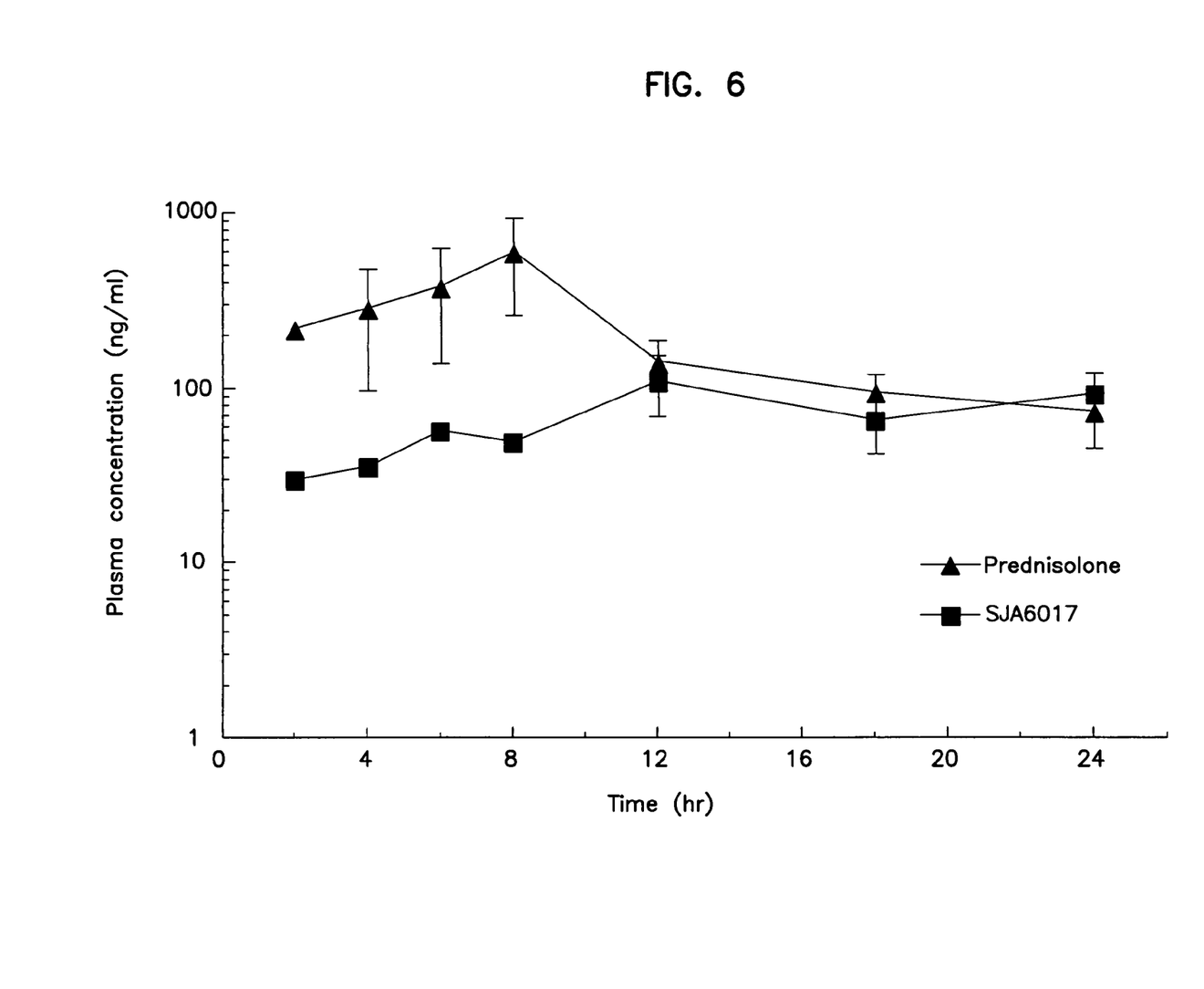
FIG. 6 is a graph showing the profile of plasma concentration of the drugs after applying pharmaceutical preparations containing prednisolone or SJA6017.

Table 7 below and FIG. 6 show the profiles of plasma concentration of prednisolone and N-(4-fluorophenylsulfonyl)-L-valyl-L-leucinal. (SJA6107) after application of the aforementioned transdermal patches (10 cm$^2$) indicated above as Nos. P5 and S5, respectively, which contained one of those drugs, to the skin of the animals. After the application, the plasma concentration of the drugs gradually rose and reached the peaks at 8 and 12 hours after application for prednisolone and SJA6017, respectively. Though the concentration of the drugs gradually lowered afterwards, substantial concentration of the drugs was noted even 24 hours after the application, when SJA6017 concentration, in particular, was still maintained at about 85% of itspeak.

TABLE 7

| | SJA6017 | | | Prednisolone | | |
|---|---|---|---|---|---|---|
| Time (hr) | Plasma concentration | SD | n | Plasma concentration | SD | n |
| 0 | 0 | 0 | 5 | 0 | 0 | 5 |
| 2 | 30 | 5 | 6 | 220 | 233 | 16 |
| 4 | 36 | 7 | 2 | 288 | 190 | 5 |
| 6 | 58 | 28 | 6 | 385 | 245 | 15 |
| 8 | 50 | 19 | 2 | 608 | 344 | 7 |
| 12 | 114 | 56 | 9 | 148 | 43 | 7 |
| 18 | 68 | 24 | 4 | 99 | 25 | 4 |
| 24 | 98 | 8 | 5 | 77 | 30 | 5 |

Unit: ng/ml (2) Intraocular concentration of prednisolone (in vivo test-1)

Prednisolone amount was determined in the plasma and the eyeball of the rats to which were applied a 3% prednisolone-containing preparation, P5. As a result, 70 ng/g prednisolone was detected 6 hours after the application of the preparation. This indicates that prednisolone was transferred to the interior of the eye at a concentration that was equivalent to 18% of the plasma concentration (Table 8). As all the samples were collected at a time, 6 hours after the application, because it was necessary to combine multiple eyes for extraction due to the minute amount of ocular tissues, no measurement could be made at any other point.

(3) Plasma and intraocular concentration of SJA6017 (in vivo test-2)

Table 8 shows the concentration of SJA6017 in the eyeball and in the plasma after the application of the SJA6017-containing transdermal patches, in comparison with corresponding values after intravenous administration of SJA6017. Also included in the table are the results of prednisolone transdermal administration in the above in vivo test-1.

TABLE 8

|  | SJA6017 transdermal application | SJA6017 intravenous injection | Prednisolone transdermal application |
|---|---|---|---|
| Point of measument | 12 hourrs after application | 15 minutes after intravenous injection | 6 hours after application |
| Plasma concentration [ng/ml] | 47 ± 12 | 120 ± 16 | 385 |
| Intraocular concentration [ng/g eye] | 7.2 | 16 | 70 |
| Eyeball/plasma ratio [Intraocular concentration, itemized] | 16% | 13% | 18% |
| Aqueous humor [ng/ml] | not detected | not detected | — |
| Lens [ng/g tissue] | 1.1 (2.3%)[*2] | not detected | — |
| Other ocular tissues[*1] [ng/g tissues] | 13.8 (29.6%)[*2] | 33.4 (27.8%)[*2] | — |

[*1]Other ocular tissues: cornea, sclera, iris-ciliary body, vitreous body, retina-choroid
[*2]Ratio to plasma concentration (100%)

Table 8 shows that 7.2 ng/g of SJA6017 was detected in the eyeball 12 hours after the application of the SJA6017-containing preparation. This value reaches about 16% of the plasma concentration of the drug, and is higher than the corresponding value (13%) detected after intravenous application. This indicates continuous nature of absorption of SJA6017 from the patch and that this method of administration of a drug by transdermal patches is a method available to continuously transfer a drug from the plasma into the eyeball.

The drug was detected in other parts of the eyeball than the aqueous humor. Among the parts other than the aqueous humor, drug transfer was higher in the tissues including the iris-ciliary body, the vitreous body, the retina-choroid. These results indicate that a transdermal patch is a suitable form for long-term application of a drug to intraocular tissues.

[Examples]

The present invention is described in further detail with reference to examples. It is not intended, however, that the present invention be limited to the examples.

<Example 1> Acrylic patches

Acrylic patches containing 5 W/W % (0.15 g) of a drug (prednisolone or SJA6017) and 30 W/W % (0.9 g) of polyoxyethylene oleyl ether (NOFABLE EAO-9905: NOF CORPORATION) as a percutaneous absorption enhancer in the drug-containing layer were prepared according to the following formula. Briefly, prednisolone and about 1.0 ml of toluene was mixed and sonicated for about 30 seconds in a disposable cup to dissolve or disperse the drug. Polyoxyethylene oleyl ether was added to this and mixed well. Then, 5.0 g of the acrylic adhesive (PE-300: NIPPON CARBIDE INDUSTRIES CO., INC.), which served as a dispersion base, and 0.2 g of the coagulation agent (CK-401: NIPPON CARBIDE INDUSTRIES CO., INC.) were added in this order and mixed well. The mixture wad degasses, spread over a release membrane with a doctor knife or a baker applicator (JAPAN APPLIED TECHNOLOGY), and left stand until the organic solvent evaporated. A lining film was placed over this, glued to it with pressure using a roller, and put in a thermostatic chamber at about 40° C. for 8–12 hours to cross-linking to take place.

(Formula)

| Drug | 0.15 g |
| Polyoxyethylene oleyl ether | 0.9 g |
| Acrylic adhesive (PE-300) | 5.0 g |
| Coagulation enhancer (CK-401) | 0.2 g |
| Toluene | 1.0 ml |

<Example 2> Acrylic patches

Acrylic patches containing 10 W/W % (0.3 g) of a drug (prednisolone or SJA6017) and 20 W/W % (0.6 g) of polyoxyethylene oleyl ether (NOFABLE EAO-9905: NOF CORPORATION) as a percutaneous absorption enhancer in the drug-containing layer were prepared in the same manner as in Example 1 according to the following formula.

(Formula)

| Drug | 0.3 g |
| Polyoxyethylene oleyl ether | 0.6 g |
| Acrylic adhesive (PE-300) | 5.0 g |
| Coagulation enhancer (CK-401) | 0.2 g |
| Toluene | 1.0 ml |

<Example 3> Acrylic patches

Acrylic patches containing 15 W/W % (0.45 g) of a drug (prednisolone or SJA6017) and 20 W/W % (0.6 g) of polyoxyethylene oleyl ether (NOFABLE EAO-9905: NOF CORPORATION) as a percutaneous absorption enhancer in the drug-containing layer were prepared in the same manner as in Example 1 according to the following formula.

(Formula)

| Drug | 0.45 g |
| Polyoxyethylene oleyl ether | 0.6 g |
| Acrylic adhesive (PE-300) | 5.0 g |
| Coagulation enhancer (CK-401) | 0.2 g |
| Toluene | 1.0 ml |

<Example 4> Acrylic patches

Acrylic patches containing 5 W/W % (0.15 g) of a drug (prednisolone or SJA6017), 10 W/W % (0.3 g) of polyoxyethylene oleyl ether (NOFABLE EAO-9905: NOF CORPORATION), and 20 W/W % (0.6 g) isopropyl myristate in the drug-containing layer were prepared in the same manner as in Example 1 according to the following formula.

(Formula)

| | |
|---|---|
| Drug | 0.15 g |
| Polyoxyethylene oleyl ether | 0.3 g |
| Isopropyl myristate | 0.6 g |
| Acrylic adhesive (PE-300) | 5.0 g |
| Coagulation enhancer (CK-401) | 0.2 g |
| Toluene | 1.0 ml |

<Example 5> Acrylic patches

Acrylic patches containing 10 W/W % (0.3 g) of a drug (prednisolone or SJA6017), 20 W/W % (0.6 g) of polyoxyethylene oleyl ether (NOFABLE EAO-9905: NOF CORPORATION), and 10 W/W % (0.3 g) isopropyl myristate in the drug-containing layer were prepared in the same manner as in Example 1 according to the following formula.

(Formula)

| | |
|---|---|
| Drug | 0.3 g |
| Polyoxyethylene oleyl ether | 0.6 g |
| Isopropyl myristate | 0.3 g |
| Acrylic adhesive (PE-300) | 5.0 g |
| Coagulation enhancer (CK-401) | 0.2 g |
| Toluene | 1.0 ml |

<Example 6> Silicone-based patches

Silicone-based patches containing 5 W/W % (0.33 g) of a drug (prednisolone or SJA6017) and 20 W/W % (1.34 g) of polyoxyethylene oleyl ether (NOFABLE EAO-9905: NOF CORPORATION) as a percutaneous absorption enhancer in the drug-containing layer were prepared according to the following formula. Briefly, prednisolone and polyoxyethylene oleyl ether were mixed well in a disposable cup and, after addition of about 2.5 ml of ethyl acetate, sonicated for about 30 seconds to dissolve or disperse the drug. To this were added 0.25 g of silicone oil (360 medical fluid, 20 cs: DOW CORNING ASIA), 4.5 g of a silicone elastomer (SLASTIC MDX4-4210, medical grade: DOW CORNING ASIA), and 0.25 g of a curing agent (curing agent for SLASTIC MDX4-4210: DOW CORNING ASIA) in the order and mixed well. The mixture was degassed, spread over a backing liner (Cerafeel #25) with a doctor knife or a baker applicator (JAPAN APPLIED TECHNOLOGY), left stand for 1 hour at room temperature, allowed to cure at 40° C., and cut into a predetermined size to give silicone-based transdermal patches.

(Formula)

| | |
|---|---|
| Drug | 0.33 g |
| Polyoxyethylene oleyl ether | 1.34 g |
| Silicone elastomer | 4.5 g |
| Silicone oil | 0.25 g |
| Curing agent | 0.25 g |
| Ethyl acetate | 2.5 ml |

<Example 7> Silicone-based patches

Silicone-based patches containing 10 W/W % (0.83 g) of a drug (prednisolone or SJA6017) and 30 W/W % (2.5 g) of polyoxyethylene oleyl ether (NOFABLE EAO-9905: NOF CORPORATION) as a percutaneous absorption enhancer in the drug-containing layer were prepared in the same manner as in Example 6 according to the following formula (Formula)

| | |
|---|---|
| Drug | 0.83 g |
| Polyoxyethylene oleyl ether | 2.5 g |
| Silicone elastomer | 4.5 g |
| Silicone oil | 0.25 g |
| Curing agent | 0.25 g |
| Ethyl acetate | 2.5 ml |

<Example 8> Silicone-based patches

Silicone-based patches containing 10 W/W % (0.83 g) of a drug (prednisolone or SJA6017), 10 W/W % (0.83 g) of polyoxyethylene oleyl ether (NOFABLE EAO-9905: NOF CORPORATION) and 20 W/W % (1.67 g) of isopropyl myristate in the drug-containing layer were prepared in the same manner as in Example 6 according to the following formula.

(Formula)

| | |
|---|---|
| Drug | 0.83 g |
| Polyoxyethylene oleyl ether | 0.83 g |
| Isopropyl myristate | 1.67 g |
| Silicone elastomer | 4.5 g |
| Silicone oil | 0.25 g |
| Curing agent | 0.25 g |
| Ethyl acetate | 2.5 ml |

<Example 9> Silicone-based patches

Silicone-based patches containing 15 W/W % (1.15 g) of a drug (prednisolone or SJA6017), 10 W/W % (0.77 g) of polyoxyethylene oleyl ether (NOFABLE EAO-9905: NOF CORPORATION) and 10 W/W % (0.77 g) of isopropyl myristate in the drug-containing layer were prepared in the same manner as in Example 6 according to the following formula.

(Formula)

| Drug | 1.15 g |
|---|---|
| Polyoxyethylene oleyl ether | 0.77 g |
| Isopropyl myristate | 0.77 g |
| Silicone elastomer | 4.5 g |
| Silicone oil | 0.25 g |
| Curing agent | 0.25 g |
| Ethyl acetate | 2.5 ml |

<Example 10> Styrene-isoprene-styrene copolymer-based patches

Styrene-isoprene-styrene copolymer-based patches containing 5 W/W % (0.15 g) of a drug (prednisolone or SJA6017) and 30 W/W % (0.9 g) of polyoxyethylene oleyl ether (NOFABLE EAO-9905: NOF CORPORATION) as a percutaneous absorption enhancer in the drug-containing layer were prepared according to the following formula. Briefly, 0.9 g of styrene-isoprene-styrene copolymer (CARIFLEX TR-1107: SHELL CHEMICAL) was dissolved in 1.05 g of liquid paraffin at about 100° C. To this were added the drug and polyoxyethylene oleyl ether and mixed well. The mixture was spread over a backing liner (Cerafeel #25) with a doctor knife or a bake applicator (JAPAN APPLIED TECHNOLOGY), and cut into a predetermined size to give styrene-isoprene-styrene copolymer-based transdermal patches.

(Formula)

| Drug | 0.15 g |
|---|---|
| Polyoxyethylene oleyl ether | 0.9 g |
| Styrene-isoprene-styrene copolymer | 0.9 g |
| Liquid paraffin | 0.15 g |

<Example 11> Styrene-isoprene-styrene copolymer-based patches

Styrene-isoprene-styrene copolymer-based patches containing 5 W/W % (0.15 g) of a drug (prednisolone or SJA6017), 20 W/W % (0.6 g) of polyoxyethylene oleyl ether (NOFABLE EAO-9905: NOF CORPORATION) and 10 W/W % (0.3 g) of isopropyl myristate in the drug-containing layer were prepared in the same manner as in Example 10 according to the following formula.

(Formula)

| Drug | 0.15 g |
|---|---|
| Polyoxyethylene oleyl ether | 0.6 g |
| Isopropyl myristate | 0.3 g |
| Styrene-isoprene-styrene copolymer | 0.9 g |
| Liquid paraffin | 0.15 g |

INDUSTRIAL APPLICABILITY

The present invention provides pharmaceutical preparations for administration of drugs for treating diseases of the posterior segment of the eye, which preparation will make it easier to achieve improved patients' compliance, and minimize burden on the patients, and eliminate unnecessary patients' risks.

What is claimed is:

1. An ophthalmic transdermal patch for treating diseases of the posterior segment of the eye comprising a drug-containing layer uniformly containing in a base matrix 20 W/W % of polyoxyethylene oleyl ether and 10–20 W/W % of isopropyl myristate as percutaneous absorption enhancers and a drug to be delivered to at least a part of the posterior segment of the eye including the lens, the vitreous body, the choroid and the retina.

2. The ophthalmic transdermal patch of claim 1 wherein the drug is an anti-cataract agent, an anti-inflammatory agent, an anti-viral agent, an immunosuppressant, a calcium channel antagonist, a glutamate receptor antagonist or a cysteine protease inhibitor.

3. The ophthalmic transdermal patch of claim 1 wherein the base matrix comprises acrylic adhesive, silicone elastomer or styrene-isoprene-styrene copolymer.

4. The ophthalmic tansdermal patch of claim 1 wherein the drug is a steroidal drug.

5. The ophthalmic transdermal patch of claim 1 wherein the drug is a compound of the formula (1)

or a pharmaceutically acceptable salt thereof, wherein $R^1$ denotes C1–C4 alkyl, or C6–C10 aryl which may be substituted, $R^2$ and $R^3$ are the same or different from each other and denote hydrogen or C1–C4 alkyl, or are combined to form a C3–C7 ring, and $R^4$ denotes aryl, cycloalkyl, or a lower alkyl which may be substituted with an aromatic heterocyclic ring.

6. The ophthalmic transdermal patch of claim 5 wherein the drug is N-(4-fluorophenylsulfonyl)-L-valyl-L-leucinal or a pharmaceutically acceptable salt thereof.

7. A method for treating a disease of at least a part of the posterior segment of the eye including the lens, the vitreous body, the choroid and the retina in an animal including a human, wherein the method comprises applying to the animal a transdermal patch comprising a drug-containing layer uniformly containing in a base matrix an effective amount of a drug to be delivered to the part and 10 W/W % of polyoxyethylene oleyl ether and 10–20 W/W % of isopropyl myristate as percutaneous absorption enhancers.

8. The method of claim 7 wherein the drug is an anti-cataract agent, an anti-inflammatory agent, an anti-viral agent, an immunosuppressant, a calcium channel antagonist, a glutamate receptor antagonist or a cysteine protease inhibitor.

9. The method of claim 7 wherein the base matrix comprises acrylic adhesive, silicone elastomer or styrene-isoprene-styrene copolymer.

10. The method of claim 7 wherein the drug is a steroidal drug.

11. The method of claim 7 wherein the drug is a compound of the formula (1)

(I)

(I)

or a pharmaceutically acceptable salt thereof, wherein $R^1$ denotes C1–C4 alkyl, or C6–C10 aryl which may be substituted, $R^2$ and $R^3$ are the same or different from each other and denote hydrogen or C1–C4 alkyl, or are combined to form a C3–C7 ring, and $R^4$ denotes aryl, cycloalkyl, or a lower alkyl which may be substituted with an aromatic heterocyclic ring.

12. The method of claim 11 wherein the drug is N-(4-fluorophenylsulfonyl)-L-valyl-L-leucinal or a pharmaceutically acceptable salt thereof.

13. An ophthalmic transdermal patch for treating diseases of the posterior segment of the eye comprising a drug-containing layer uniformly containing in a base matrix 20 W/W % of polyoxyethylene oleyl ether and 10–20 W/W % of isopropyl myristate as percutaneous absorption enhancers and a drug to be delivered to at least a part of the posterior segment of the eye including the lens, the vitreous body, the choroid and the retina, wherein the drug is a steroidal drug or a compound of the formula (1)

or a pharmaceutically acceptable salt thereof, wherein $R^1$ denotes C1–C4 alkyl, or C6–C10 aryl which may be substituted, $R^2$ and $R^3$ are the same or different from each other and denote hydrogen or C1–C4 alkyl, or are combined to form a C3–C7 ring, and $R^4$ denotes aryl, cycloalkyl, or a lower alkyl which may be substituted with an aromatic heterocyclic ring.

14. The ophthalmic transdermal patch of claim 13 wherein the base matrix comprises acrylic adhesive, silicone elastomer or styrene-isoprenestyrene copolymer.

15. The ophthalmic transdermal patch of claim 13 wherein the drug is N-(4-fluorophenylsulfonyl)-L-valyl-L-leucinal or a pharmaceutically acceptable salt thereof.

16. The ophthalmic transdermal patch of claim 13 wherein the steroidal drug is prednisolone.

\* \* \* \* \*

UNITED STATES PATENT AND TRADEMARK OFFICE
CERTIFICATE OF CORRECTION

| | | |
|---|---|---|
| PATENT NO. | : 7,052,714 B1 | Page 1 of 1 |
| APPLICATION NO. | : 10/089431 | |
| DATED | : May 30, 2006 | |
| INVENTOR(S) | : Tojo et al. | |

It is certified that error appears in the above-identified patent and that said Letters Patent is hereby corrected as shown below:

Front page, (54) Title: "ADSORPTION" should read --ABSORPTION--

Figure 7:
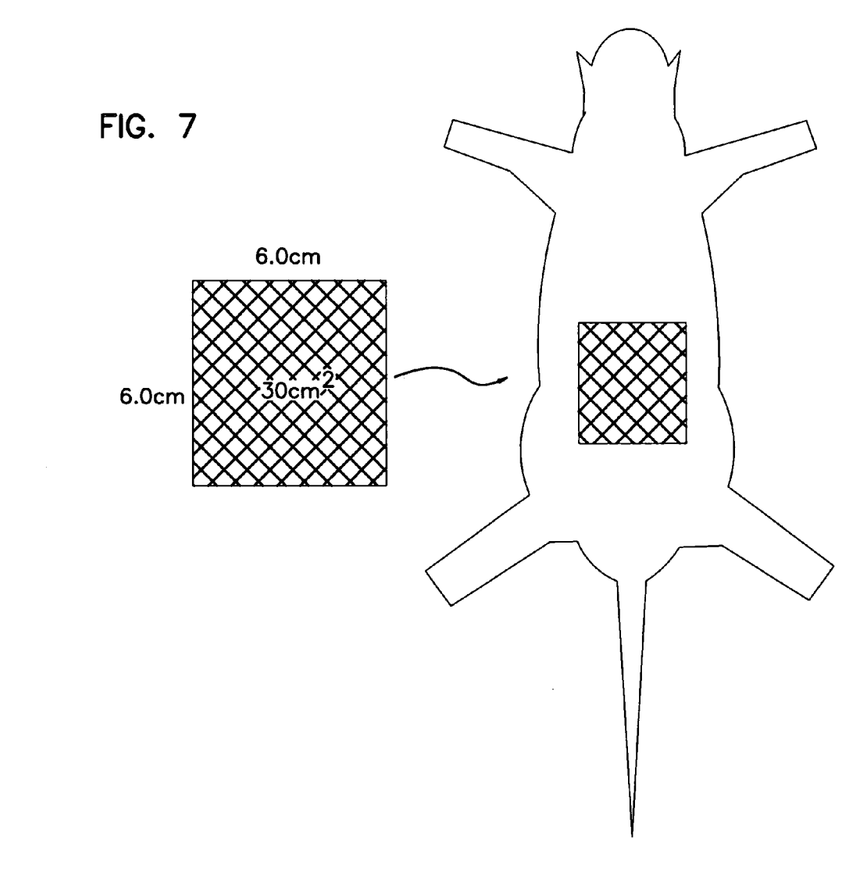
FIG. 7 is a schematic illustration of the shape of a SJA6017-containing patch and a rat to which the patch is applied.

Drawings, Sheet 7 of 7 (Fig. 7): The horizontal line is incorrect. "6.0cm" should read --5.0cm--. The correct drawing is shown below:

Col. 18, line 51, claim 7: "and 10 W/W %" should read --and 20 W/W %--

Signed and Sealed this

Twenty-first Day of November, 2006

JON W. DUDAS
*Director of the United States Patent and Trademark Office*

UNITED STATES PATENT AND TRADEMARK OFFICE
CERTIFICATE OF CORRECTION

PATENT NO. : 7,052,714 B1  Page 1 of 1
APPLICATION NO. : 10/089431
DATED : May 30, 2006
INVENTOR(S) : Tojo et al.

It is certified that error appears in the above-identified patent and that said Letters Patent is hereby corrected as shown below:

Front page, (54) Title: "ADSORPTION" should read --ABSORPTION--

Drawings, Sheet 7 of 7 (Fig. 7): The horizontal line is incorrect. "6.0cm" should read --5.0cm--. The correct drawing is shown below:

Col. 18, line 51, claim 7: "and 10 W/W %" should read --and 20 W/W %--

This certificate supersedes Certificate of Correction issued November 21, 2006.

Signed and Sealed this

Second Day of January, 2007

JON W. DUDAS
*Director of the United States Patent and Trademark Office*